(12) United States Patent
Vivek et al.

(10) Patent No.: US 8,127,614 B2
(45) Date of Patent: Mar. 6, 2012

(54) METHODS AND SYSTEMS FOR ULTRASONIC COUPLING USING ULTRASONIC RADIATION PRESSURE

(75) Inventors: Vibhu Vivek, Santa Clara, CA (US); Babur Hadimioglu, Angelholm (SE); Ratnakar Dadi, San Jose, CA (US)

(73) Assignee: Microsonic Systems Inc., San Jose, CA (US)

( * ) Notice: Subject to any disclaimer, the term of this patent is extended or adjusted under 35 U.S.C. 154(b) by 414 days.

(21) Appl. No.: 12/418,496

(22) Filed: Apr. 3, 2009

(65) Prior Publication Data
US 2009/0249877 A1    Oct. 8, 2009

Related U.S. Application Data

(60) Provisional application No. 61/042,556, filed on Apr. 4, 2008.

(51) Int. Cl.
*G01N 29/024* (2006.01)
*G01N 29/036* (2006.01)
(52) U.S. Cl. .................. 73/644; 73/579; 73/597; 702/54
(58) Field of Classification Search .................... 73/644, 73/596, 597, 601, 579, 609, 643; 702/54
See application file for complete search history.

(56) References Cited

U.S. PATENT DOCUMENTS
3,934,460 A    1/1976  Sherwin et al.
(Continued)

FOREIGN PATENT DOCUMENTS
WO    WO-2009124289 A2    10/2009
WO    WO-2009124290 A1    10/2009
WO    WO2009149701    * 12/2009

OTHER PUBLICATIONS

"International Application Serial No. PCT/US2009/039547, Search Report mailed Jul. 23, 2009", 3 pgs.
(Continued)

*Primary Examiner* — J M Saint Surin
(74) *Attorney, Agent, or Firm* — Schwegman, Lundberg & Woessner, P.A.

(57) ABSTRACT

Apparatus and methods for ultrasonic coupling using ultrasonic radiation pressure generating are provided. Ultrasonic energy is generated to propagate in the form of ultrasonic waves in a medium coupled to a second element. The ultrasonic energy is converged in the medium to couple the medium to an object located at a distance from the second element. Additional apparatus and methods are disclosed.

28 Claims, 4 Drawing Sheets

U.S. PATENT DOCUMENTS

| | | | |
|---|---|---|---|
| 4,033,178 A | | 7/1977 | Holt et al. |
| 4,455,873 A | * | 6/1984 | Abts .................... 73/629 |
| 4,646,573 A | * | 3/1987 | Stoll .................... 73/606 |
| 4,773,267 A | * | 9/1988 | Abts .................... 73/597 |
| 4,787,070 A | * | 11/1988 | Suzuki et al. .......... 367/140 |
| 5,041,849 A | | 8/1991 | Quate et al. |
| 5,278,028 A | | 1/1994 | Hadimioglu et al. |
| 5,469,744 A | | 11/1995 | Patton et al. |
| 5,669,971 A | | 9/1997 | Bok et al. |
| 5,983,723 A | | 11/1999 | Buckin et al. |
| 6,364,454 B1 | | 4/2002 | Hadimioglu |
| 6,368,482 B1 | | 4/2002 | Oeftering et al. |
| 6,666,541 B2 | | 12/2003 | Ellson |
| 6,682,214 B1 | | 1/2004 | Vivek et al. |
| 6,948,843 B2 | | 9/2005 | Laugharn, Jr. et al. |
| 7,080,557 B2 | | 7/2006 | Adnan |
| 2005/0061078 A1 | * | 3/2005 | Miller et al. |
| 2009/0249866 A1 | | 10/2009 | Vivek |
| 2009/0254289 A1 | | 10/2009 | Vivek et al. |

OTHER PUBLICATIONS

"International Application Serial No. PCT/US2009/039547, Written Opinion mailed Jul. 23, 2009", 7 pgs.

Ellson, Richard, et al., "Transfer of low nanoliter volumes between microplates using focused acoustics—automation considerations", *Journal of the Association for Laboratory Automation*, 8(5), (Oct. 2003), 29-34.

Elrod, S. A, et al., "Nozzleless droplet formation with focused acoustic beams", *J. Appl. Phys. 65*, (1989), 3441-3447.

Farnow, S. A, "Aocustic Applications of the Zone Plate", *Ph.D Dissertation, Stanford University*, (1976), 152 pgs.

Hadimioglu, B., et al., "Acoustic ink printing", *IEEE Ultrasonics Symposium*, 1992, *Proceedings*, (1992), 929-935.

Hadimioglu, B., et al., "Acoustic ink printing: an application of ultrasonics for photographic quality printing at high speed", *2001 IEEE Ultrasonics Symposium*, (2001), 627-635.

Oeftering, R. C, "Improving plating by use of intense acoustic beams", *NASA Tech Briefs*, (Mar. 2003), 2 pgs.

Vivek, V., et al., "Novel acoustic-wave micromixer", *Proc. IEEE Int. Micro Electro Mechanical Syst. Conf.*, (2000), 668-673.

Hadimioglu, B., et al., "High-efficiency Fresnel acoustic lenses", *IEEE Ultrasonics Symposium*, 1993. *Proceedings*, (1993), 579-582.

Zou, Q., et al., "Water Needle—A new phenomenon for ink-jet printing", *IEEE 2001 International Conference on Solid-State Sensors and Actuators*, (2001), 6 pgs.

* cited by examiner (PRIOR ART)
FIG. 1

METHODS AND SYSTEMS FOR ULTRASONIC COUPLING USING ULTRASONIC RADIATION PRESSURE

RELATED APPLICATIONS

This patent application claims the benefit of priority under 35 U.S.C. Section 119(e), to U.S. Provisional Patent Application Ser. No. 61/042,556, filed on Apr. 4, 2008, which is incorporated herein by reference in its entirety.

BACKGROUND

Devices utilizing ultrasonic waves at megahertz (MHz) frequencies are used in many applications such as ultrasonic non-destructive evaluation of sample materials, ultrasonic imaging, ultrasonic ink printing, ultrasonic mixing, droplet dispensing for pharmaceutical and biological applications, and selective coating or plating of materials on substrates.

In virtually all of the above-mentioned applications, the core of the system consists of an ultrasonic transducer that converts electrical signals into ultrasonic signals and vice versa. The ultrasonic transducer is typically a piezoelectric plate formed between two metal electrodes. Other forms of ultrasonic transducers are also known in the art and may be used in various applications of ultrasonic energy.

BRIEF DESCRIPTION OF THE DRAWINGS

Some embodiments of the disclosed technology are illustrated by way of example and not limitation in the figures of the accompanying drawings in which.

DETAILED DESCRIPTION

Example apparatus and methods for ultrasonic coupling using ultrasonic radiation pressure will be described. In the following description for the purpose of explanation, numerous examples having example-specific details are set forth to provide an understanding of example embodiments. It will be evident, however, to one skilled in the art that the present examples may be practiced without these example-specific details, and/or with different combinations of the details than are given here.

Some example embodiments described herein may include applying electromagnetic waves generated by an electromagnetic radiation source (e.g., a radio frequency (RF) source) coupled to an ultrasonic transducer to generate ultrasonic energy. The ultrasonic energy may propagate in the form of ultrasonic waves. The ultrasonic energy may be converged (e.g., focused) in a medium (e.g., a fluid) coupled to a second element (e.g., an ultrasonic converging element). The converging may result in coupling the medium to an object (e.g., a sample object) located at a distance from the second element.

The radio frequency source may, for example, generate an RF signal in the form of a tone-burst with a typical frequency range of 0.1-1000 MHz. The signal may be suitably amplified, and then applied between the electrodes of the ultrasonic transducer (also referred to, hereinafter, as transducer). The transducer may convert the electrical energy of the RF signal into the ultrasonic energy in the form of ultrasonic signals that are directed towards the sample object. Depending on the application and particular design, the transducer may be attached onto a buffer layer (e.g., an insulating layer) on one side, typically towards the sample object, and onto a backing material on the opposing side. Again depending on the application, a suitable ultrasonic converging element (also known as ultrasonic lens, hereinafter called converging element) may be formed on the transducer to concentrate the ultrasonic energy over a selected area of the sample object that retains a sample.

The form of the sample object depends on the particular application. In applications such as non-destructive evaluation or ultrasonic imaging, it is typically a solid material that can be examined by the ultrasonic signals. In fluidic applications such as mixing, the sample object is typically an industry standard micro-well plate that holds the sample, e.g., fluid solvents that will be agitated by the ultrasonic signals. The micro-well plate typically has a relatively thin bottom to allow for efficient transmission of the ultrasonic waves into the sample. The fluid solvents may also contain particulates or solids to be mixed, as well. In yet other biological applications, the sample may be placed on glass slides.

In virtually all of the applications described above, the sample object may be free to move, because the sample object is scanned relative to the transducer (e.g., in imaging applications), or, in fluidic applications, it can to be brought in and out of the instrument quickly, once the desired function (e.g., mixing or fluid transfer) is accomplished. The sample object is typically placed from a few millimeters to several centimeters away from the transducer assembly, near the zone where the ultrasonic energy may be concentrated.

Because air and virtually all gases do not transmit ultrasonic waves at megahertz frequencies efficiently, a medium (e.g., a coupling fluid, typically water) is applied between the transducer and the sample object to couple the ultrasonic energy (e.g., ultrasonic waves) efficiently between the transducer and the sample. In some of the applications described above, it is usually not desired to immerse all of the transducer and sample assemblies into the coupling fluid. In order to provide reliable liquid contact between the transducer and the sample object such that the contact would not be lost over time due to the evaporation of the coupling fluid, a mechanism that continuously replenishes the coupling fluid between the transducer and the sample object may be used.

Such assemblies are commonly referred to as "bubbler" assemblies (see, for example, Olympus NDT Inc., immersion transducer catalog).

Figure 1:
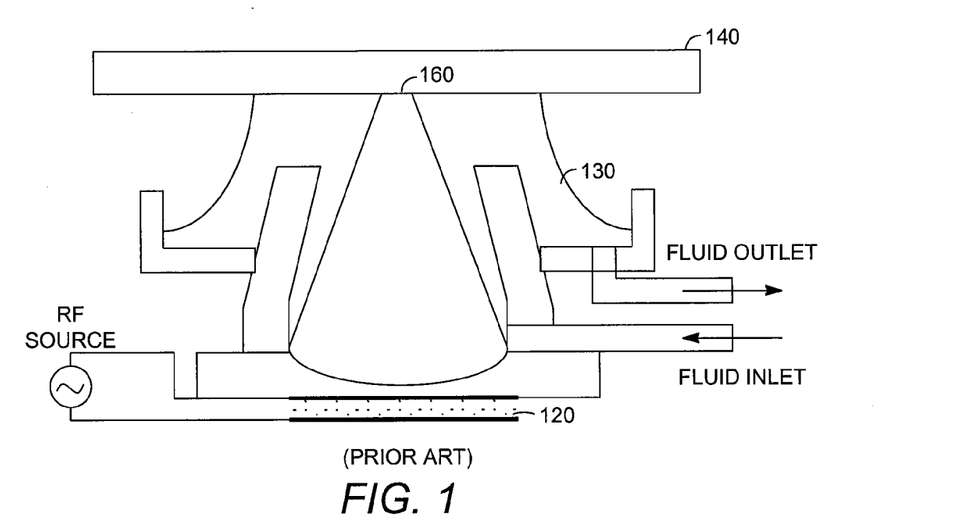
FIG. 1 is a diagram illustrating a cross-section of a prior art ultrasonic device, including a coupling mechanism known as a bubbler.

FIG. 1 is a diagram illustrating a cross-section of a prior art ultrasonic device 100, including a coupling mechanism known as a bubbler. The cross-section shown in FIG. 1 is made through the fluid inlet and outlet. The bubbler mechanism commonly used in many ultrasonic applications has several potentially undesired attributes. It requires a mechanical pump to re-circulate the coupling fluid 130 between a transducer 120 and a sample object 140, which adds further cost and complexity to the instrument. In addition, the mechanical pump is a potential source of instrument failure. The relatively high flow rate of the coupling fluid is a potential source of overflows and resultant catastrophic failures. In typical bubbler assemblies, it is not possible to precisely control a contact area 160 of the coupling fluid 130 with the sample object 140, and the contact area 160 may spread over parts of the sample object 140 that may not be desired to wet with the coupling fluid 130 (as removing the coupling fluid may require extensive drying operations).

Furthermore, there is always a possibility of having trapped air bubbles that prevent efficient transfer of ultrasonic energy between the transducer 120 and the sample object 140. In addition, in some biological applications, it may be desired to use micro-well plates that have a non-flat bottom to reduce a "dead" volume of liquid sample. When such plates are used with current bubbler assemblies, it may not be practical or possible to achieve ultrasonic contact (e.g., a contact that provides efficient coupling of the ultrasonic energy) with the bottom of the micro-well plate. Non-flat bottom micro-well plates are typically more prone to trapped air bubbles. Some example embodiments, as described herein, may address these potential problems in the designs employing bubbler assemblies in ultrasonic applications.

Ultrasonic waves propagating through a medium produce a steady (DC) pressure in the medium known as "radiation pressure". When ultrasonic fields are applied through a fluid towards a "free" surface (e.g., fluid/air interface), the ultrasonic radiation pressure produced is simply given by $P_{rad}=2$ I/c, where I is the intensity of the ultrasonic beam (e.g., the ultrasonic waves) and c is the speed of sound in the fluid. If the intensity of the ultrasonic beam is high enough, the force exerted on the fluid surface by the radiation pressure causes the fluid surface to rise to form a fluid mound (see, for example, fluid mound 320 in FIG. 3) in the area where the ultrasonic beam is applied. Such fluid motion has been used in the past to generate small droplets from the fluid, at the tip of the mound, in applications like ultrasonic ink printing (see, for example, S. A. Elrod, et. al. "Nozzleless Droplet Formation with Focused Ultrasonic Beams," J. Appl. Phys. 65, 3441, 1989).

In example embodiments described in this application, a force applied on the fluid surface by the ultrasonic radiation pressure and the subsequent rise of a cone of the fluid is used to provide efficient ultrasonic coupling between the transducer, the coupling fluid assembly, and the sample object. This may improve or replace the bubbler and associated re-circulating fluid flow assemblies. In addition, if there are bubbles trapped within the coupling fluid, the radiation pressure may be used to dislodge these bubbles to improve the efficiency of the ultrasonic coupling between the transducer and the sample retained in the sample object.

Figure 2:
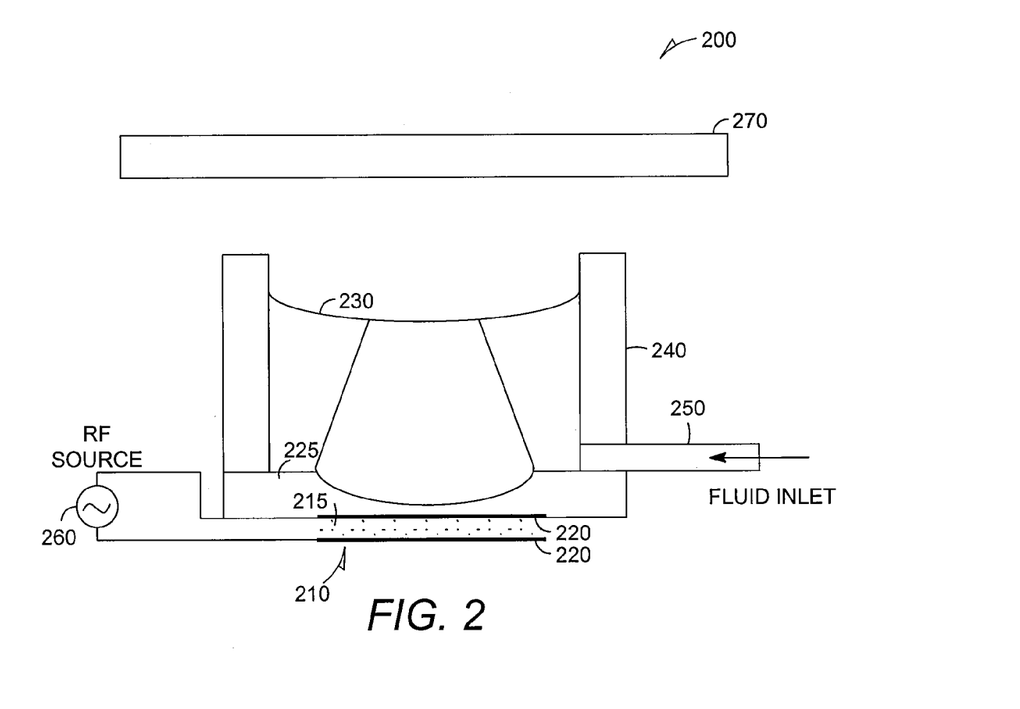
FIG. 2 is a diagram illustrating a cross-section of an example apparatus for ultrasonic coupling using ultrasonic radiation pressure, according to various embodiments of the invention.

FIG. 2 is a diagram illustrating a cross-section of an example apparatus 200 for ultrasonic coupling using ultrasonic radiation pressure, according to various embodiments of the invention. The cross-section shown in FIG. 2 is made through the fluid inlet 250. The structure shown in FIG. 2 is a basic structure of the apparatus 200 and depicts a status of a coupling fluid 230 (e.g., water) prior to the application of an RF signal generated by the RF source 260 into a transducer 210. The transducer may be coupled to the RF source 260 (e.g., an electromagnetic radiation source) and configured to generate ultrasonic energy to propagate in the form of ultrasonic waves in the coupling fluid 230. The apparatus 200 may also include a second element (e.g., a focusing element 225) coupled to a medium (e.g., the coupling fluid 230). The focusing element 225 may converge the ultrasonic energy (e.g., ultrasonic waves) in the coupling fluid 230 to couple the coupling fluid 230 to an object (e.g., sample object) 270 located at a distance from the focusing element 225.

The sample object 270, that the ultrasonic waves couple to, may be positioned such that a surface to receive the ultrasonic energy is near the nominal focal distance of the transducer 210 (e.g., a distance from the transducer 210, where the ultrasonic energy is converged), typically at a distance of a few tenths of millimeters to several centimeters in many ultrasonic applications. A coupling fluid filling mechanism may control a flow of the coupling fluid 230 from the fluid inlet 250 into a fluid container 240. The flow may be controlled such that the top surface of the coupling fluid 230 is below the sample object 270, without making contact. This filling mechanism may also contain features to replenish the coupling fluid 230 to keep the top surface of the coupling fluid 230 near a pre-determined level, as the coupling fluid 230 may be lost due to evaporation over time.

The converging element 225 may include an ultrasonic lens, an array of lenses, a Fresnel-type lens, or an array of Fresnel-type lenses. In example embodiments, the Fresnel-type lens may be formed by configuring one or both of electrodes 220 formed on an ultrasonic sensor plate 215 (e.g., a plate of piezoelectric material). The electrodes 220 may be formed by coating or otherwise applying one or more layers of a conductive material (e.g., copper, aluminum, silver, gold, conductive polymers, etc.). The RF signal from the RF source 260 may be applied to the electrodes 220 of the transducer 210. The application of the RF pulse may induce an ultrasonic radiation pressure inside the coupling fluid 230, resulting in lifting the top surface of the coupling fluid 230.

Figure 3:
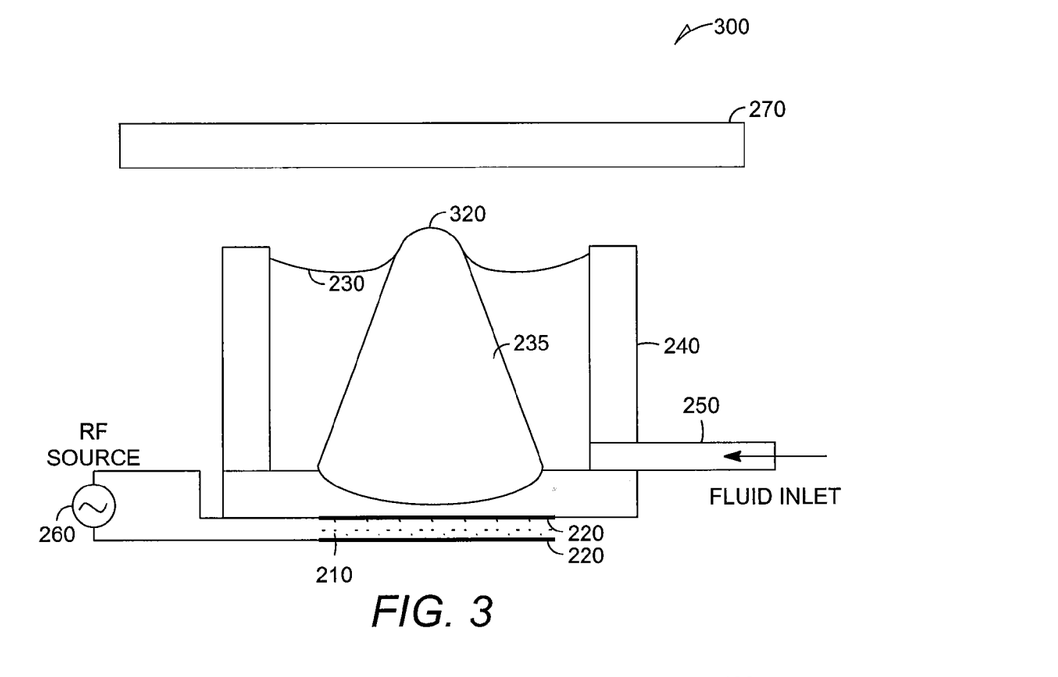
FIG. 3 is a diagram illustrating an example operation mode of the apparatus of FIG. 2, where a fluid mound is rising as a result of ultrasonic radiation pressure, according to various embodiments of the invention.

FIG. 3 is a diagram illustrating an example operation mode 300 of the apparatus 200 of FIG. 2, where a fluid mound 320 is rising as a result of ultrasonic radiation pressure, according to various embodiments of the invention. In the operation mode 300 shown in FIG. 3, following the application of an RF signal of sufficient amplitude and duration to the transducer 210, the top surface of the coupling fluid 230 may be lifted to form a fluid mound 320. The formation of the fluid mound 320 is a result of the induced ultrasonic radiation pressure at portion 235 of the coupling fluid 230, where the ultrasonic waves are concentrated. However, the energy of RF signal applied to the transducer 210 is not quite enough to raise the fluid mound 320 sufficiently such that the fluid mound 320 of coupling fluid 230 makes contact with the sample object 270. When the amplitude and/or the duration of the RF signal is increased, the surface of the fluid may rise further.

Figure 4:
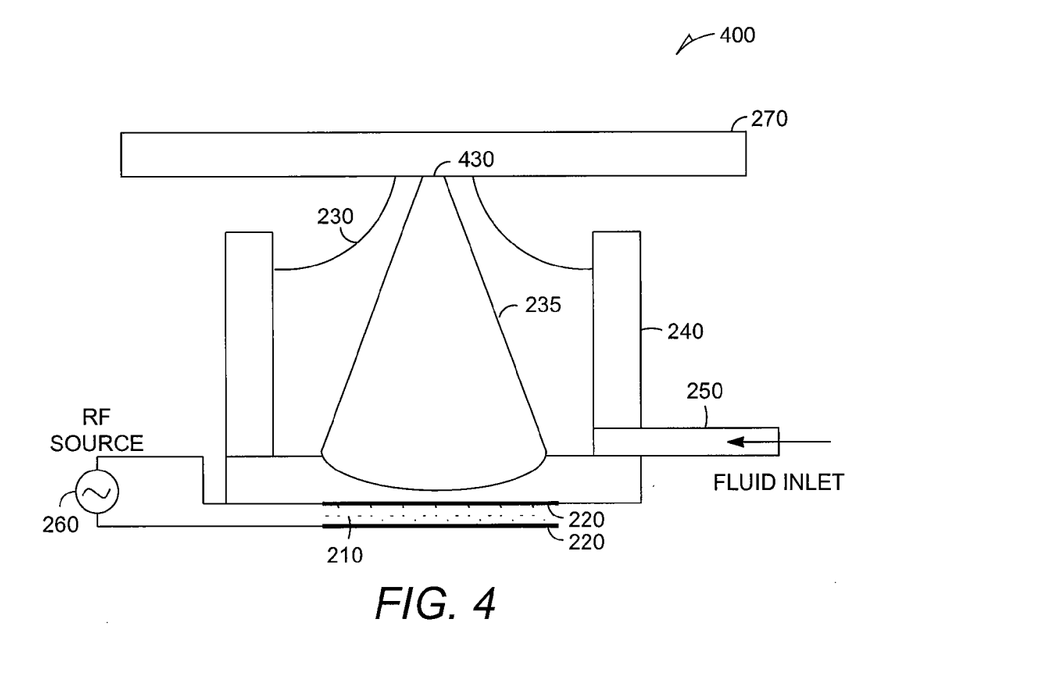
FIG. 4 is a diagram illustrating an example operation mode of the apparatus of FIG. 2, where a fluid mound is brought into contact with an object as a result of ultrasonic radiation pressure, according to various embodiments of the invention.

FIG. 4 is a diagram illustrating an example operation mode 400 of the apparatus 200 of FIG. 2, where a fluid mound 320 is brought into contact with an object 270 as a result of ultrasonic radiation pressure, according to various embodiments of the invention. In the state of operation mode 400, the amplitude and the duration of the RF pulse applied to the transducer 210 is adjusted such that the top of the raised area (e.g., the fluid mound 320 of FIG. 3) of the coupling fluid 230 makes contact with the sample object 270. The contact area 430 may provide an efficient means of coupling the concentrated ultrasonic waves (portion 235) into the sample object 270.

Using the example apparatus 200 and operation mode 400 described above to provide ultrasonic coupling between the transducer 210 and the sample object 270, it may be possible to obtain a more precisely defined contact area of coupling fluid 230 with the sample object 270. This feature may not be available in the conventional bubblers (see FIG. 1) used in the current state of art. Furthermore, it may be possible to avoid wetting of the parts of the sample object 270 that are not desired to have fluid contact. By adjusting the ultrasonic energy delivered by the ultrasonic waves (e.g., through adjustment of the amplitude and/or the duration of the RF signal applied to the transducer), it may be possible to finely adjust the contact area 430. In the apparatus 200 described herein, there are no mechanical pumps working at flow rates that might be prone to catastrophic failures.

Once the coupling fluid 230 makes contact with the sample object 270, the coupling fluid may maintain contact with the sample object 270, or it may take quite a while for the coupling fluid 230 to break contact with the sample object 270. The contact between the coupling fluid 230 and the sample object 270 may hold, even after the RF pulse is turned off, due to the inertia of the coupling fluid motion and the capillary forces between the sample object 270 and the coupling fluid 230.

When a surface-lifting waveform applied to the RF source 260 is turned off, after a surface-lifting period is over and while the coupling fluid 230 is still in contact with the sample object 270, it may be possible to excite the transducer 210 with an impulse or tone-burst waveforms (depending on the particular application) to provide a desired functionality with the device. Such functionalities may include examining the sample surface with ultrasonic signals reflected from the surface for ultrasonic imaging applications or mixing fluids in a micro-well plate for ultrasonic mixing applications. When desired (e.g., when the contact between the coupling fluid 230 and the sample object 270 is lost after a certain period of time), the surface lifting period may be repeated periodically to sustain long-term contact of the coupling fluid 230 with the sample object 270.

Figure 5:
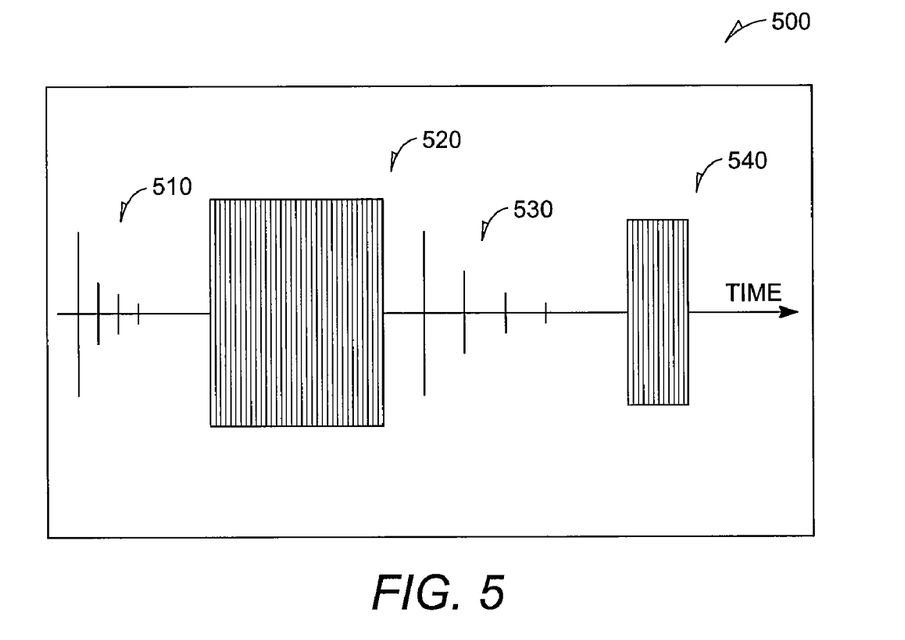
FIG. 5 is a diagram illustrating example waveforms of signals used in various phases of operation of the apparatus of FIG. 2, according to various embodiments of the invention.

FIG. 5 is a diagram illustrating example waveforms 500 of signals used in various phases of operation of the apparatus 200 of FIG. 2, according to various embodiments of the invention. The signals may be generated by the RF source 260 of FIG. 2 and applied to the electrodes 220 of FIG. 2 to energize (e.g., excite) the transducer 210 of FIG. 2. The signals may assume various waveforms depending on the application. For example, the waveform 520 may represent a surface-lifting pulse that may be used to provide coupling between the coupling fluid 230 and the sample object 270 via ultrasonic radiation pressure. The duration of the surface-lifting pulse (e.g., a time period to lift the fluid surface) may be sufficiently long and its amplitude may be sufficiently high for the fluid mound 320 of FIG. 3 to rise to contact the sample object 270 to couple the coupling fluid 230 to the sample object 270.

The time period may be controlled to provide a long-term contact between the fluid surface and the sample object 270. For example, the surface-lifting pulses may be applied for multiple time periods to provide the long-term contact between the fluid surface and the sample object 270. The pre-mound interrogation pulses 510 may be applied prior to the application of the surface-lifting pulse to obtain information related to the position of the surface of the coupling fluid 230 (e.g., track a level of a peak of the fluid mound 320) while at rest (e.g., prior to the application of the ultrasonic radiation pressure on the surface).

The information obtained may include attributes of an echo signal reflected from the peak of the fluid mound 320. The attributes of the echo signal may be measured to verify contact between the fluid surface and the sample object 270. The attributes of the echo signal may include amplitude, a delay time, or a phase. The information obtained can be used by a feedback mechanism to control the inlet of the coupling fluid 230 into the coupling fluid container 240 of FIG. 2, such that the fluid level at rest is at or near a desired location. In an alternative example embodiment, the information may be used to control amplitude or duration of the RF pulses generated by the RF source 260.

According to example embodiments, post-mound interrogation pulses 530 may be applied after the surface-lifting waveform to measure the time delay of the echoes from the top surface of the coupling fluid 230 of FIG. 3 (as in typical sonar applications). Using such a measurement, it may be possible to track the position of the top of the fluid mound 320 of FIG. 3 and determine whether the fluid mound 320 has risen sufficiently to make contact with the sample object 270. The information obtained can be used in a suitable feedback application to precisely determine the amount of the ultrasonic energy used to provide contact with the sample object 270. In other words, the apparatus 200 can be made self-calibrating to reach a desired level of the ultrasonic coupling.

There is also further information available to provide positive confirmation of the contact of the fluid with the sample object 270. One such information can be gathered from the amplitude of the echoes from the top of the fluid mound 320 in response to the post-mound interrogation pulses 530. Prior to the contact of the coupling fluid 230 to the sample, the echo amplitudes should be relatively large because the liquid/air interface results in near total reflection.

Once the coupling fluid 230 makes contact, the echo shows a discrete drop in amplitude, since part of the ultrasonic energy in the interrogating pulse is coupled into the sample object 270. Another manner to gather contact information is to monitor the phase of the echoes. The phase of the echoes may show a 180-degree reversal once the contact between the coupling fluid 230 and the sample object 270 is achieved, since the reflection coefficient of ultrasonic waves between a liquid-air interface is negative, whereas the coefficient is positive for reflections between a liquid and virtually all solids. Once the coupling fluid 230 is in contact with the sample object 270 the apparatus 200 is in standard mode of operation and a signal represented by a waveform 540 may be applied to the electrodes 220 of the transducer 210 of FIG. 2 to perform a desired functionality (e.g., imaging, mixing, droplet dispensing, etc).

The described example embodiments may offer significant potential advantages in instruments that operate with an array of transducers and focusing elements, typically used in biological or pharmaceutical applications that involve liquid manipulation over a multitude of fluid samples using focused ultrasonic energy. Some examples of such devices and their applications are described in the concurrently submitted Application entitled "Methods to Form High Efficiency and Uniform Fresnel Lens Arrays for Ultrasonic Liquid Manipulation." (incorporated herein by reference in its entirety).

Figure 6:
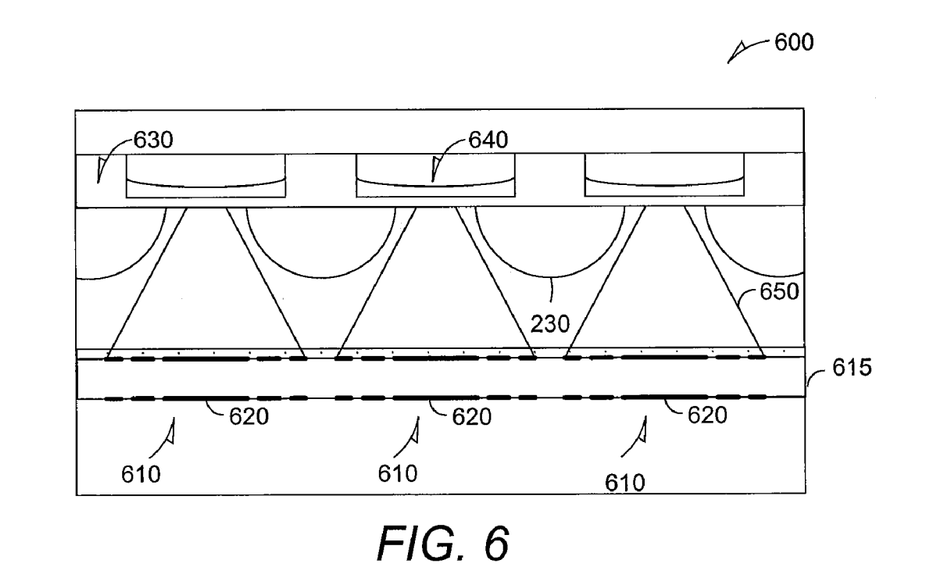
FIG. 6 is a diagram illustrating an example operation of an apparatus for ultrasonic coupling using ultrasonic radiation pressure, according to various embodiments of the invention.

FIG. 6 is a diagram illustrating an example operation of an apparatus 600 for ultrasonic coupling using ultrasonic radiation pressure, according to various embodiments of the invention. The apparatus 600 includes an array of Fresnel-type ultrasonic transducers 610 that generate and focus the ultrasonic waves. The Fresnel-type ultrasonic transducers 610 are fabricated on a piezoelectric plate 615 by forming Fresnel-type focusing elements 620. The Fresnel-type focusing elements 620 are actually electrodes coated on the top and bottom sides of the piezoelectric plate 615. The electrodes may be configured, for example, in concentric rings to form Fresnel-type focusing elements 620. The fluid samples 640 to be manipulated may be contained in micro-wells of a micro-well plate 630, which is held near the nominal focal distance of the Fresnel-type focusing elements 620. The Fresnel-type focusing elements 620 may concentrate the ultrasonic energy generated by the Fresnel-type ultrasonic transducers 610.

In order to couple the ultrasonic waves to the fluid samples 640 in the micro-well plate 630, coupling fluid 230 may be applied over the transducers 610 by means not shown in FIG. 6 (see, for example, fluid inlet 250 of FIG. 2). Unlike other applications, the thickness of coupling fluid 230 is such that the coupling fluid 230 does not normally contact the bottom of the micro-well plate 630. The level of the coupling fluid 230 can be dynamic (e.g., continuously moving by re-circulating) or kept static by replenishing coupling fluid 230 only as it evaporates. As described earlier, by suitably adjusting the ultrasonic energy to raise a mound of the coupling fluid 230 over the Fresnel-type ultrasonic transducers 610, it may be possible to achieve fluidic contact with the micro-well plate 630.

The fluidic contact may be formed in the areas of the micro-well plate 630 covered by micro-wells, so that the concentrated ultrasonic energy 650 couples into the fluid samples 640 to perform the required fluid manipulations. This may allow making fluidic contacts in select areas of the micro-well plate 630 and keep the rest of the area dry to make it easier to perform plate-drying operations.

When Fresnel-type focusing elements 620 are used to focus the ultrasonic energy in conjunction with the methods described herein, a further improvement may be made in the operation of the apparatus 600 as described below. It is well-known that Fresnel-type focusing devices exhibit nearly linear-dependence of the focal length on the operating frequency (see, for example, S. A. Farnow, "Ultrasonic Applications of the Zone Plate," Ph.D. Dissertation, Stanford University (1975)). If the bandwidth of the Fresnel-type ultrasonic transducers 610 is sufficiently wide, it may be possible to adjust the operating frequency for the surface-lifting pulse (see waveform 520 of FIG. 5) such that the focus is closer to the surface of the coupling fluid 230 before the mound is raised. Such an operation may reduce the RF power for raising the mound and making fluidic contact with the micro-well plate 630. In example embodiments, this idea may even be extended further, by adjusting an RF frequency of the RF pulses (e.g., sweeping the RF frequency across a frequency range within the design bandwidth of the transducer around the design frequency within a general range of about 0.1 to 1000 MHz) as the fluid mound rises to keep the focus close to the surface of the mound to reduce the consumption of RF power used to achieve efficient ultrasonic contact with the micro-well plate 630.

Figure 7:
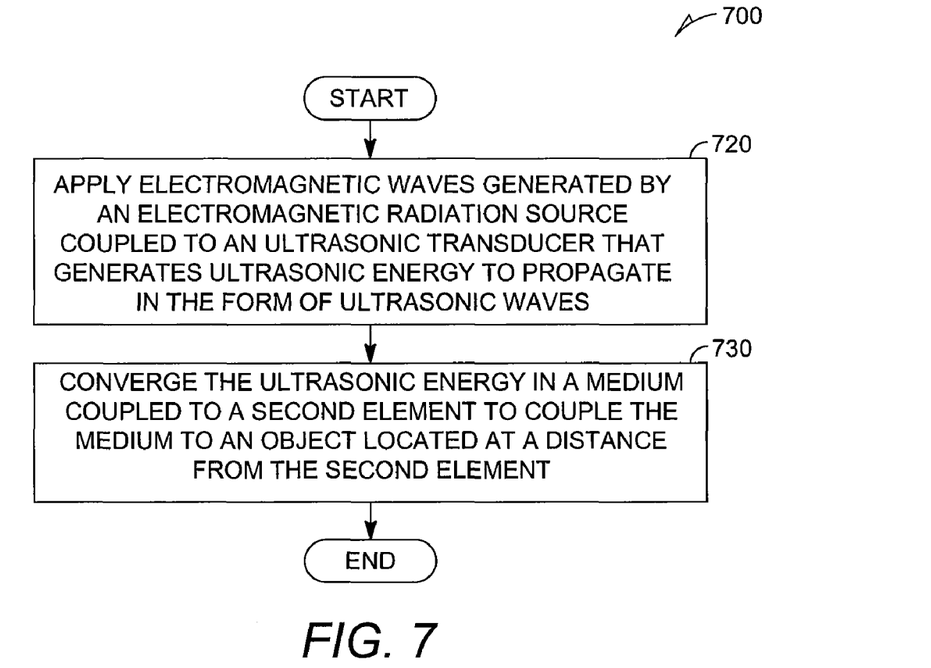
FIG. 7 is a flow diagram illustrating an example method for ultrasonic coupling using ultrasonic radiation pressure, according to various embodiments of the invention.

FIG. 7 is a flow diagram illustrating an example method 700 for ultrasonic coupling using ultrasonic radiation pressure, according to various embodiments of the invention. At operation 720, electromagnetic waves (e.g., RF pulses as represented by waveforms shown in FIG. 5) may be generated by an electromagnetic radiation source (e.g., RF source 260 of FIG. 2) and coupled to an ultrasonic transducer (e.g., ultrasonic transducer 610 of FIG. 6) to generate ultrasonic energy. The ultrasonic energy may propagate in the coupling fluid 230 of FIG. 6 in the form of ultrasonic waves.

The ultrasonic energy may be converged, at operation 730, in a medium (e.g., coupling Fluid 230 of FIG. 6) to a second element (e.g., the ultrasonic focusing elements 620) to couple the medium to an object (e.g., micro-well plate 630 of FIG. 6) located at a distance from the Fresnel-type focusing elements 620. Although the flow diagram of FIG. 7 shows an "End", the method may be performed continuously if desired.

Figure 8:
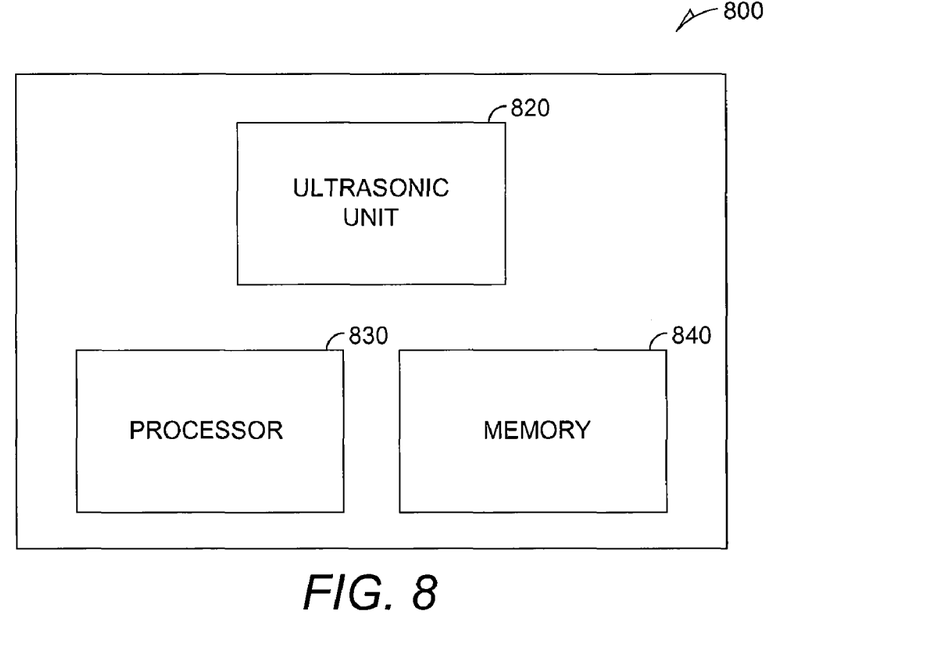
FIG. 8 is a diagram illustrating an example system for ultrasonic coupling using ultrasonic radiation pressure, according to various embodiments of the invention.

FIG. 8 is a diagram illustrating an example system 800 for ultrasonic coupling using ultrasonic radiation pressure, according to various embodiments of the invention. The system 800 may include an ultrasonic unit 820, a processor 830, and memory 840. Example embodiments of the ultrasonic unit 820 may include apparatus 200 of FIG. 2 or apparatus 600 of FIG. 6. However, the ultrasonic unit 820 may not be limited to parts and components shown in the above figures and may include auxiliary components not shown in those figures.

In example embodiments, the ultrasonic unit 820 may use the processor 830 to execute instructions (e.g., software) stored in the memory 840. The processor 830 may include a micro-processor, a central processing unit (CPU), and/or the like. The memory 840 may include rotating memory, random access memory (RAM), read-only memory (ROM), or flash type memory. The memory 840 may also store data related to the operation of the ultrasonic unit 820, for example, maintenance data, data related to samples analyzed, etc. The instructions, for example, may include software to control various parts of the ultrasonic unit 820 such as the RF source 260 of FIG. 2 or one or more pumps that may propel the coupling fluid 230 into the fluid container 240 of FIG. 2.

Although the embodiments described above show structures with the coupling medium not nominally making contact with the sample object, it is also possible to use example embodiments of the present inventive subject matter in configurations wherein the coupling fluid does make contact with the sample object, in structures similar to conventional bubbler systems (see FIG. 1). Example embodiments of the present subject matter may be utilized to improve functionality and efficiency by dislodging and/or collapsing any potential bubbles trapped between the transducer and sample objects, without using excessive forced flow of the coupling fluid with an external drive mechanism. Micro-well plates with non-flat bottoms that are used in certain biological applications are particularly prone to trapped bubbles. Hence, example embodiments of the present subject matter may improve the efficiency of coupling in those applications.

Embodiments of methods and apparatus for ultrasonic coupling using ultrasonic radiation pressure have been described. Although an embodiment has been described with reference to specific example embodiments, it will be evident that various modifications and changes may be made to these embodiments without departing from the broader spirit and scope of the inventive subject matter. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this inventive subject matter to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that allows the reader to quickly ascertain the nature of the technical disclosure. It is submitted with the understanding that it will not be used to interpret or limit the claims. In addition, in the foregoing Detailed Description, it may be seen that various features are grouped together in a single embodiment for the purpose of streamlining the disclosure. This method of disclosure is not to be interpreted as limiting the claims. Thus, the following claims are hereby incorporated into the Detailed Description, with each claim standing on its own as a separate embodiment.

What is claimed is:

1. An apparatus comprising:
   an ultrasonic transducer coupled to an electromagnetic radiation source and configured to generate ultrasonic energy to propagate in the form of ultrasonic waves; and
   a second element coupled to a medium, the second element to converge the ultrasonic energy in the medium to couple the medium to an object located at a distance from the second element, the medium comprising a fluid; and
   a fluid container formed by walls attached to the second element to contain the fluid, the ultrasonic transducer being energized by applying to the electromagnetic radiation source a radio frequency (RF) signal for a time period to lift a fluid surface level at a portion of a fluid surface to form a fluid mound.

2. The apparatus of claim 1, wherein the electromagnetic radiation source comprises a radio frequency (RF) source.

3. The apparatus of claim 1, wherein the second element comprises an ultrasonic converging element including at least one of an ultrasonic lens, an array of lenses, a Fresnel-type lens, and an array of Fresnel-type lenses.

4. The apparatus of claim 1, wherein the time period is sufficiently long for the fluid mound to rise to contact the object to couple the medium to the object, and wherein a contacted area of the object is controllable.

5. The apparatus of claim 1, wherein the ultrasonic transducer is periodically energized by applying to the electromagnetic radiation source the RF signal for multiple time periods to provide a long-term contact between the fluid mound and the object.

6. The apparatus of claim 1, wherein at an end of the time period the ultrasonic transducer is excited by applying to the electromagnetic radiation source at least one of an impulse and a tone-burst waveform.

7. The apparatus of claim 1, wherein the ultrasonic transducer is excited via applying to the electromagnetic radiation source interrogation pulses prior to the time period to track the level of the fluid surface before being lifted.

8. The apparatus of claim 1, wherein the ultrasonic transducer is excited via applying to the electromagnetic radiation source interrogation pulses after the time period to track a level of a peak of the fluid mound.

9. The apparatus of claim 8, wherein the ultrasonic transducer is excited via applying to the electromagnetic radiation source interrogation pulses after the time period, and wherein an attribute of an echo signal reflected from the peak of the fluid mound is measured to verify contact between the fluid surface and the object.

10. The apparatus of claim 9, wherein the interrogation pulses are used to detect a bubble in the medium between the second element and the object, and wherein the applied RF signal is tuned to dislodge the bubble via exerting ultrasonic radiation pressure.

11. The apparatus of claim 9, wherein the attribute of the echo signal is at least one of amplitude, a time delay, and a phase.

12. The apparatus of claim 1, wherein the second element comprises a Fresnel-type lens, and wherein a frequency of the applied RF signal is adjusted and the adjustment includes sweeping the frequency across a frequency range.

13. The apparatus of claim 1, wherein the object comprises a non-flat surface facing the medium.

14. A method comprising:
   applying electromagnetic radiation waves generated by an electromagnetic radiation source coupled to an ultrasonic transducer to generate ultrasonic energy to propagate in the form of ultrasonic waves;
   converging the ultrasonic energy in a medium coupled to a second element to couple the medium to an object located at a distance from the second element, the medium comprising a fluid contained in a fluid container formed by walls attached to the second element; and
   energizing the ultrasonic transducer by applying to the electromagnetic radiation source a radio frequency (RF) signal for a time period to lift a fluid surface level at a portion of a fluid surface to form a fluid mound.

15. The method of claim 14, wherein the applying of the RF signal is for a sufficiently long time period so that the fluid mound contacts the object to couple the medium to the object, the method further comprising controlling a contacted area of the object.

16. The method of claim 14, wherein the applying of the RF signal is for multiple time periods to provide a long-term contact between the fluid surface and the object.

17. The method of claim 14, further comprising exciting the ultrasonic transducer at an end of the time period via applying to the electromagnetic radiation source at least one of an impulse and a tone-burst waveform.

18. The method of claim 14, further comprising exciting the ultrasonic transducer via applying to the electromagnetic radiation source interrogation pulses prior to the time period to track the level of the fluid before being lifted.

19. The method of claim 14, further comprising exciting the ultrasonic transducer via applying to the electromagnetic radiation source interrogation pulses after the time period to track a level of the lifted fluid surface.

20. The method of claim 14, further comprising exciting the ultrasonic transducer via applying to the electromagnetic radiation source interrogation pulses after the time period and measuring an attribute of an echo signal reflected from the lifted fluid surface to verify contact between the fluid surface and the object.

21. The method of claim 20, wherein the attribute of the echo signal is at least one of amplitude, a time delay, and a phase.

22. The method of claim 14, wherein the second element comprises a Fresnel-type lens and the method further comprising adjusting a frequency of the applied RF signal, the adjustment including sweeping the frequency across a frequency range.

23. The method of claim 14, further comprising detecting and dislodging a bubble between the second element and the object.

24. A system comprising:
a processor;
a memory coupled to the processor;
an ultrasonic unit coupled to an object via ultrasonic radiation pressure, the ultrasonic unit comprising,
a radio frequency generator to generate radio frequency waves;
an ultrasonic transducer coupled to the radio frequency generator to convert the radio frequency waves to ultrasonic waves;
an ultrasonic converging means coupled to the ultrasonic transducer to converge the ultrasonic waves; and
a coupling fluid arranged to form an ultrasonic coupling between the ultrasonic transducer and the object resulting from formation of a fluid mound formed as a result of the ultrasonic radiation pressure induced by the ultrasonic waves.

25. An apparatus comprising:
an ultrasonic transducer coupled to an electromagnetic radiation source and configured to generate ultrasonic energy to propagate in the form of ultrasonic waves; and
a second element coupled to a medium, the second element to converge the ultrasonic energy in the medium to couple the medium to an object located at a distance from the second element, the medium comprising a fluid, and the object comprising a non-flat surface facing the medium; and
a fluid container formed by walls attached to the second element to contain the fluid, the ultrasonic transducer being energized by applying to the electromagnetic radiation source a radio frequency (RF) signal for a time period to dislodge or collapse a bubble trapped in the fluid near the non-flat surface of the object.

26. The apparatus of claim 25, wherein the ultrasonic transducer is further energized by applying to the electromagnetic radiation source at least one interrogation pulse to detect the bubble from an echo signal.

27. A method comprising:
applying electromagnetic waves generated by an electromagnetic radiation source coupled to an ultrasonic transducer to generate ultrasonic energy to propagate in the form of ultrasonic waves;
converging the ultrasonic energy in a medium coupled to a second element to couple the medium to an object located at a distance from the second element, the medium comprising a fluid contained in a fluid container formed by walls attached to the second element, and the object comprising a non-flat surface facing the medium; and
energizing the ultrasonic transducer by applying to the electromagnetic radiation source a radio frequency (RF) signal for a time period to dislodge or collapse a bubble trapped in the fluid near the non-flat surface of the object.

28. The method of claim 27, further comprising
energizing the ultrasonic transducer by applying to the electromagnetic radiation source at least one interrogation pulse to detect the bubble from an echo signal.

\* \* \* \* \*